June 4, 1946. W. H. REEVES Plant Pat. 693
APRICOT TREE
Filed Aug. 14, 1945
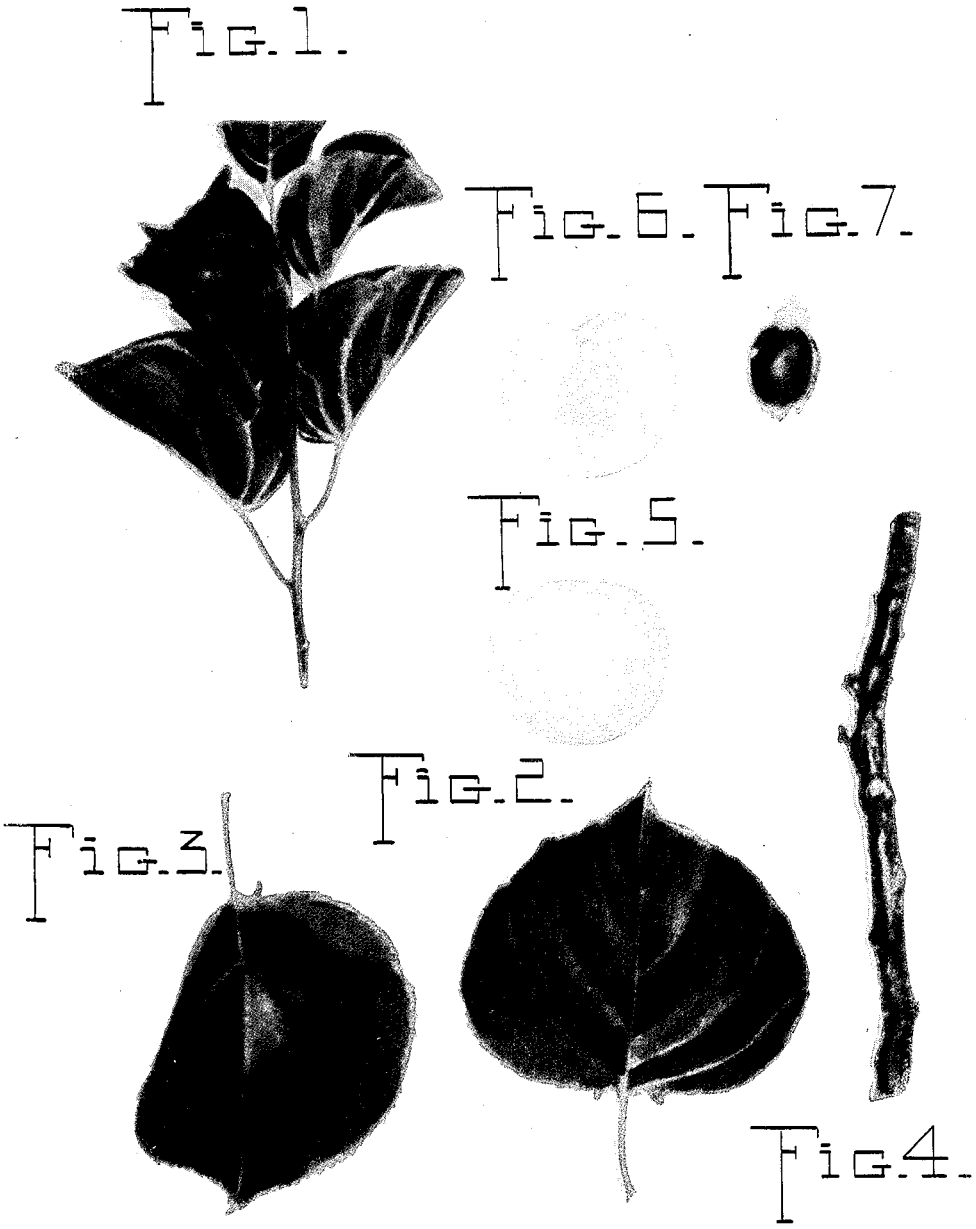
Inventor
W. H. Reeves
By: Robb & Robb
Attorneys.

Patented June 4, 1946

Plant Pat. 693

UNITED STATES PATENT OFFICE

693

APRICOT TREE

William Henry Reeves, Burbank, Calif., assignor to Armstrong Nurseries, Inc., Ontario, Calif., a corporation of California Application August 14, 1945, Serial No. 610,765

1 Claim. (Cl. 47—62)

The present discovery relates to a new and distinct variety of apricot tree, originating as a chance seedling, and having many important features distinguishing it from all other apricots now known commercially.

This new variety has been thoroughly tested by me in Southern California and its characteristics carefully compared with other Southern California varieties for the purpose of developing its distinguishing characters, singly and in combination.

Primarily, it is found to have a very early season of ripening, and the fruit is exceptionally large for such early ripening apricots.

Among other features of distinction are: the exceptionally vigorous habit of growth of the trees and the attendant large size of the leaves and stomata; a winter chilling requirement similar in grade to that of the variety commercially known as "Earligold" and shorter than that of such varities as "Newcastle," "Royal," and many of the other more common commercial varieties, making it better suited to growing in Southern California; and the production of regular crops of uniformly sized fruit each season regardless of winter temperature conditions.

The ripening season of this new variety is approximately in the same season as "Earligold," although it usually begins a few days earlier, but it differs from "Earligold" in respect to the size of the fruit, being much larger by an approximate average of 25%, and further it has a more highly developed blush in the skin than "Earligold," and is notably a much superior dessert fruit.

This new apricot differs further from "Earligold," which is a partial clingstone, in that the flesh of the fruit has a greater freedom from the stone. To the best of my knowledge, no other varieties tested in Southern California, other than "Earligold," have as low a chilling requirement as this new variety. It is further characterized by a tenderness of flesh which makes it an excellent dessert fruit with true melting quality suitable only for home planting or local market use.

Asexual reproduction shows that these characteristics hold true through succeeding propagations.

The accompanying illustrations depict the novel characteristics of the foliage and fruit of this new variety as nearly as it is possible to show the same. In the drawing:

Figure 1 shows a spray of young foliage illustrating particularly the color and form of the same;

Figures 2 and 3 are top and bottom views of a mature leaf depicting color and other characteristics;

Figure 4 is a fragmentary view of a specimen of the wood showing the large size of the lenticels constituting a feature of novelty of this variety;

Figures 5 and 6 are elevational and sectional views of the fruit; and

Figure 7 is an elevation of the seed showing the slight tendency of the flesh to adhere on the suture side near base.

The following is a detailed description of the new variety, all references to color being in accordance with the R. F. Wilson's Horticultural Colour Chart, except where indicated to be in accordance with Ridgway's Color Standards and Nomenclature:

Specimens described were grown at Burbank, California.

Dates of first and last picking: First picking usually about May 30th; last picking June 10th to June 15th in Burbank, California, ten days later at Ontario, California.

Tree: Large; vigorous; dense; hardy; very productive; regular bearer.

*Trunk.*—Medium stocky; medium smooth, but more so than "Royal."

*Branches.*—Medium stocky; medium smooth. On two-year wood, Vandyke Brown (Ridgway) Plate XXVIII. On new wood (shady side) Empire Green (Ridgway) Plate XXIII. On sunny side, near Grape Green (Ridgway) Plate XLI. *Lenticels*—numerous; large; much broader than "Royal."

*Leaves.*—Length, 7 to 10 centimeters. Width, 7 to 10 centimeters. Size, large. Ovate, very broadly ovate; nearly orbicular mucronate; abruptly pointed; thick; Danube Green (Ridgway) Plate XXXII. *Margin*—bidentate or doubly dentate to coarsely serrate. *Petiole*—medium long; 2 to 3 centimeters; medium thick. *Glands*—average number, four—from three to six. Alternate usually; large, about twice as large as "Royal"; globose; stipitate; Light Fluorite Green (Ridgway) Plate XXXII, Position—near base of leaf or end of petiole. Stipules—having one to two—linear—oblong in shape with crenate edge — teeth on petiole side.

*Flower-buds.*—Medium size; medium long.

*Flowers.*—Dates first and full bloom—March 10th to 20th usually, depending on severity of winter. Medium size; early to medium compared with other varieties; White or nearly so.

3

Fruit: Maturity when described—June 15, 1945.

*Size.*—Variable; large. Axial diameter—2" average. Transverse in suture plane—2⅛" average. At right angles to suture plane—1¾" average.

*Form.*—Uniform; symmetrical; near globose; oblate slightly, particularly at the base; compressed laterally. *Suture*—shallow; extends from base to beyond but discontinuous at apex. *Ventral surface*—rounded slightly; strongly lipped on both sides from base to halfway to apex. More slightly lipped on remaining portion of ventral surface. *Cavity*—elongated on one side; depth—approximately $\frac{3}{16}$"; breadth—¼" x ⅜"; markings—none. *Base*—rounded to elongated. *Apex*—rounded to slightly depressed. Pistil point slightly depressed. *Stem*—length, approximately ¼"; medium to stout. Adherence to stone—strong to medium.

*Skin.*—Thin; tender; tenacious to flesh. *Tendency to crack*—slight, none in dry season. *Color*—Majolica Yellow, Plate 09, p. 102, modified by a blush of Rose Madder, Plate 23/2, p. 23, Ch. II, in a varying degree depending on the exposure of the fruit to the sun. *Down*—moderate; short; does not roll up when rubbed.

*Flesh.*—*Color*—Persimmon Orange, Chart 1, 710/3, around outside edge; Apricot, Chart 1, 609, center; around pit Saffron Yellow, Chart 1, 7/3, page 7, at cross sectional view. *Surface of pit cavity*—*Persimmon Orange*, Chart 1, 710/2. *Juice*—abundant; rich. *Texture*—medium firm; fine; melting. *Fibres*—few; coarse; tender. *Ripens*—uneven; earliest at apex. *Flavor*—subacid; mild. *Aroma*—not pronounced. *Eating quality*—good.

Stone:—Free. Adheres to flesh slightly on suture side near base.

*Fibres.*—Short; retains short fibre-like threads along ventral ridge.

4

*Size.*—Medium.

*Length.*—1" to 1⅛".

*Breadth.*—¾" to ⅝".

*Thickness.*—⅛" to $\frac{9}{16}$".

*Form.*—Narrowly oval; slightly cuneate toward apex.

*Base.*—Straight; hilum, oval; apex, rounded.

*Sides.*—Equal; curved on right and left sides. *Surface*—regular; pitted throughout very slightly. Two furrows on suture side deeper at base but very shallow at apex end.

*Ridges.*—Rounded on dorsal but sharp on suture side.

*Embryo.*—Slightly elongated. *Ventral edge*—thick without wing toward base. *Dorsal edge*—full with no groove throughout. Ridge on seed coat on dorsal side from base to apex. *Color of stone*—(dry stone) Ochroceous Buff, (Ridgway) Plate XV. *Tendency to split*—strong, but cracks easily. Embryos that have not dried are thick at basal end and narrowing at apex end, somewhat thicker on suture side than dorsal side.

Use: Local; dessert.

Keeping quality: Medium.

Resistance to: Insects—good to medium; diseases—good as to shot-hole fungus on fruit.

Shipping quality: Medium to poor.

I claim:

A new and distinct variety of apricot tree characterized as to novelty by the early ripening season of the fruit and exceptionally large size for such early varieties; the highly developed blush in the skin of the fruit and its excellent quality for dessert purposes, and tenderness of the flesh; by the unusually vigorous habit of growth of the trees and the attendant large size of leaves and stomata; the very low chilling requirement; and regular production each season of crops of uniform size fruit regardless of winter temperature conditions, substantially as shown and described.

WILLIAM HENRY REEVES.